(12) United States Patent
Schepis et al.

(10) Patent No.: US 9,855,124 B2
(45) Date of Patent: Jan. 2, 2018

(54) HYDRO PULSE WATER FLOSSER WITH RESERVOIR

(71) Applicants: Jason F. Schepis, Rochelle Park, NJ (US); James Wickstead, Mendham, NJ (US)

(72) Inventors: Jason F. Schepis, Rochelle Park, NJ (US); James Wickstead, Mendham, NJ (US)

(73) Assignee: J.F.S. Innovations, LLC, Rochelle Park, NJ (US)

( * ) Notice: Subject to any disclaimer, the term of this patent is extended or adjusted under 35 U.S.C. 154(b) by 542 days.

(21) Appl. No.: 14/215,698

(22) Filed: Mar. 17, 2014

(65) Prior Publication Data

US 2014/0261534 A1   Sep. 18, 2014

Related U.S. Application Data

(60) Provisional application No. 61/793,135, filed on Mar. 15, 2013.

(51) Int. Cl.
*A61C 17/02* (2006.01)
*A61H 13/00* (2006.01)
*A61C 17/028* (2006.01)

(52) U.S. Cl.
CPC ........ *A61C 17/0214* (2013.01); *A61C 17/028* (2013.01); *A61H 13/005* (2013.01)

(58) Field of Classification Search
CPC .. A61H 9/0007; A61H 9/0021–9/0028; A61H 33/6057; A61H 2201/5051; A61C 17/00–17/028; A61C 1/0061; A61C 1/0084; A61C 15/00; A61C 3/025; B05B 1/083; B05B 3/04; B05B 15/00; B05B 15/1627; B05B 15/066
USPC .................................. 4/567, 615, 443, 420.4
See application file for complete search history.

(56) References Cited

U.S. PATENT DOCUMENTS

| | | | |
|---|---|---|---|
| 4,991,569 A | 2/1991 | Martin | |
| 5,027,798 A | 7/1991 | Primiano | |
| 5,082,444 A * | 1/1992 | Rhoades | A61C 17/02 239/389 |
| 5,218,956 A * | 6/1993 | Handler | A61C 17/0214 433/80 |
| 5,220,914 A | 6/1993 | Thompson | |
| 5,484,281 A | 1/1996 | Renow | |
| 6,238,178 B1 * | 5/2001 | Stearne | F01D 15/06 137/99 |
| 6,245,032 B1 * | 6/2001 | Sauer | A61C 17/02 433/80 |
| 7,117,867 B2 * | 10/2006 | Cox | A61M 15/0065 128/200.14 |
| 7,314,456 B2 | 1/2008 | Shaw | |
| 7,814,585 B1 | 10/2010 | Reich | |
| 8,047,840 B2 | 11/2011 | Shaw | |
| 2009/0082706 A1 | 3/2009 | Shaw | |

(Continued)

*Primary Examiner* — Rachel Young
(74) *Attorney, Agent, or Firm* — Baldini Law, LLC; Jack B. Baldini, Esq.

(57) ABSTRACT

The present invention provides an advanced water flosser utilizing a direct water source, such as, but not limited to, an attachment to a shower head, that also may embody a reservoir and/or compartment capable of introducing other desirable substances designed to enhance the teeth cleaning process, such as, but not limited to fluoride, antibiotics, mouthwash, whiteners and the like.

9 Claims, 13 Drawing Sheets

(56) References Cited

U.S. PATENT DOCUMENTS

2009/0124945 A1    5/2009  Reich
2011/0117517 A1*   5/2011  Bergheim .............. A61C 5/02
                                                          433/81

* cited by examiner

HYDRO PULSE WATER FLOSSER WITH RESERVOIR

This application claims priority to Provisional U.S. Patent Application Ser. No. 61/793,135, filed Mar. 15, 2013.

FIELD OF THE INVENTION

The present invention provides an advanced water flosser utilizing a direct water source, such as, but not limited to, an attachment to a shower head, implementing a hydro pulse mechanism that also may embody a reservoir and/or compartment capable of introducing other desirable substances designed to enhance the teeth cleaning process, such as, but not limited to fluoride, antibiotics, mouthwash, whiteners and the like.

BACKGROUND

Periodontitus and gingivitis are diseases of the gums that are easily combated with proper oral care. Physical brushing is often recommended to stimulate the gums and also reduce plaque and remove food particles. Unfortunately, brushing involves bristles, and bristle brushes vary in design effectiveness, bristle hardness and change and deform with age, thus losing efficacy. Additionally, bristles can be irritating to some mouths and gums. Typical bristle brushes are also generally not effective at cleaning between teeth.

Other products that allow physical removal of food particulate from between teeth are known. For example, toothpicks and flossing thread are well documented. Water based flossing devices are a relatively recent addition to oral healthcare. Typically, water based flossing devices incorporate an electric motor which deliver a steady stream of water, but may also provide pulsed water. None of these devices however, provide a pulsing stream of aerated water or the capability of delivering a simultaneous whitening option or other choice of, or combination of, tooth and gum health substances in a convenient, mess free, desirable application.

Dental hygiene tools adapted for use by attaching to shower heads are known. For example, U.S. Pat. No. 4,991,569 discloses an oral hygiene shower nozzle apparatus wherein a shower nozzle is provided with an aperatured dispersion plate integrally and orthogonally formed to a rear portion of the nozzle with a rotating valve plate rotatably mounted parallel to and adjacent a rear face of the dispersion plate whereupon alignment of the respective apertures effects water dispersion at a forward portion of the nozzle. Rotation of the valve plate to misalign the apertures of the respective valve plate and nozzle effects water directed through a conduit to an adjoining oral hygiene tool for the cleansing of teeth by use of a conically valved dental applicator nozzle formed with an elongate flexible tube fixedly secured to the nozzle assembly rearwardly of the valve plate. Furthermore, a toothpick and dental floss holder is provided.

In another example, U.S. Pat. No. 5,027,798 discloses a dental water jet flossing apparatus comprises an elongated, flexible tubing attached at one of its ends directly to a household water supply, preferably at a point where water temperature can be controlled, as at the water outlet pipe mounting a shower head. The opposite end of the tubing is connected to a hand-held unit that is configured to releasably mount a dental water jet nozzle. A water flow control valve is included in the hand unit and configured to engage the flexible tubing and selectively constrict the latter to various desired degrees to selectively control the amount and rate of water delivered through the tubing and hence expelled from the nozzle. A syphon cup containing mouthwash or the like may be provided in-line to meter desired fluids into the water being delivered out of the nozzle and into the user's mouth.

In another example, U.S. Pat. No. 5,220,914 discloses an apparatus especially effective in dislodging plaque from the teeth through the application of a mixture of a liquid oral antiseptic with water under pressure. In a preferred embodiment to be described, the apparatus is connected for use between the showerhead and the water supply to the head, with the amount of pressure controllable through the apparatus via a valve which serves to mix the antiseptic and water together. A second valve is employed as part of the applicator to dislodge the plaque and which operates to pulsate the admixture to the teeth under manual user control. In a second embodiment, the plaque dislodging apparatus is coupled within a bathroom vanity, or otherwise beneath a countertop, coupling the apparatus between the water supply source and the faucet or tap.

In another example, U.S. Pat. No. 5,484,281 discloses a shower mounted dental hygiene device, which consists of a multipurpose direction valve to direct water flow to a shower head, dental hygiene device or both, a pulsating device, a dentifrice introduction device and an ergodynamically designed handle having a quick attachment device for interchanging dental hygiene attachments.

In another example, U.S. Pat. No. 7,314,456 discloses a valve for adjusting the flow of water through an oral irrigation device connected to a shower head located on a handle connected to a water-dispensing syringe or pick. Rotation of the valve controls the amount and pressure of water dispensed through the syringe or pick in a direct stream from the shower head.

In another example, U.S. Pat. No. 7,814,585 discloses a show [sic] head water pick apparatus includes a first pipe segment for attachment to a shower pipe protruding outwardly from shower stall wall and having a first pipe segment outward end; a switch valve having a switch valve intake end connected to the first pipe segment outward end, and having a shower head output branch to which a shower head is connected and a water pick output branch, and having a valve operation handle for delivering water flow alternately to the shower head and to the water pulsing and pick assembly; a water pulsing unit connected to the water pick output branch; a water pick tube having a tube first end and a tube second end, the tube first end being connected to the water pulsing unit; and a water pick secured to the tube second end.

In another example, U.S. Pat. No. 8,047,840 discloses a valve for adjusting the flow of water through an oral irrigation device is connected to a shower head by a flexible conduit. The valve is located on a handle connected to a water-dispensing pick for cleaning teeth and gums. Mixing apparatus is provided for injecting a secondary fluid, such as a mouthwash, into the flexible conduit upstream from the pick in a direct stream from the shower head.

In another example, U.S. Patent Application US 2009/0082706 discloses a valve for adjusting the flow of water through an oral irrigation device is connected to a shower head by a flexible conduit. The valve is located on a handle connected to a water-dispensing pick for cleaning teeth and gums. An impeller-type pump is provided in the flexible conduit to pulsate the water.

In another example, U.S. Patent Application US 2009/0124945 discloses a pulsating water pick used in combination with a pulsating showerhead supplied with pressurized water. The showerhead includes rotatable impeller periodically blocking water flow to a fixed regulator plate having circumferentially spaced apart groups of holes. A rotatable control plate-showerhead ejector face plate therebeneath has at least one opening sized to expose one group of holes. Raised lands limit water flow between adjacent plates and depressed areas lead to peripheral shower holes in a peripheral channel. The control plate rotates and plate openings expose hole groups in one mode, but in another, holes are blocked and water flows to depressed areas and the peripheral shower holes in the peripheral channel. The improved pulsating water pick includes a water passage port formed in the control plate and the showerhead ejector face plate, a coupler thereat leading to a tube, a water pick handle and a pick nozzle.

Therefore, there remains an unmet need for the device of the present invention that provides a hand held, hydraulic oral care product that provides a hydro pulsed, aerated and concentrated water stream originating from a single consistent water source and concentrates it into a stream of variable high pressure water specifically integrated with other desirable substances to improve overall tooth and gum health and appearance.

SUMMARY OF THE INVENTION

The present invention provides a hand held, hydraulic oral care product that attaches to any consistent water source to provide an operator chosen hydro pulsed, aerated and concentrated water stream of variable high pressure focused water capable of integrating with operator chosen substances, such as fluoride, antibiotics, whiteners and the like, for delivery of a tooth and gum health and appearance optimized water cleaning mechanism.

BRIEF DESCRIPTION OF THE DRAWINGS

FIG. 1 shows the basic structural components of one embodiment of the device of the present invention. The water source is connected to the water line-in (1) and the water flow is allowed into the device of the present invention by a valve (2). A reservoir or other substances container (not shown here) is attached and controlled by separate valves (3, 4). The hydro-pulse mechanism (5 and detailed below), nozzle valve (6), rotator (7) and nozzle (8) are shown.

FIGS. 3A and 3B show a view of one embodiment of the hydro-pulse mechanism of the device of the present invention. In one embodiment, FIG. 3A, the water flow is divided by a Y-line (18) so that water flows directly into both the hydro wheel chamber and the pulse chamber. In one embodiment, FIG. 3B, the hydro wheel chamber is formed with a housing (13) containing a paddle wheel (12), a cover (11), a water inlet (16) and a water outlet (17). In one embodiment, the water is contained in the hydro wheel chamber by the wall of the pulse wheel (14) which is also contained within the housing (13) to create the pulse flow through the nozzle (8) with water being contained in the pulse chamber with a cover (15).

FIG. 4A shows a view of the partially assembled mechanism with the cover (11) removed. FIGS. 4B and 4C show alternate orientations of the pulse wheel. FIG. 4A shows one embodiment of the paddle wheel (12). FIG. 4B shows one embodiment of the external view of the hydro-pulse mechanism showing the relationship between the paddle wheel chamber (13A) and the pulse wheel chamber (13B). FIG. 4C shows an internal view of the hydro-pulse mechanism showing the relationship of the paddle wheel (12) within its chamber and the pulse wheel (14) within its chamber and the connection along an axis (12A).

DETAILED DESCRIPTION

Figure 1:
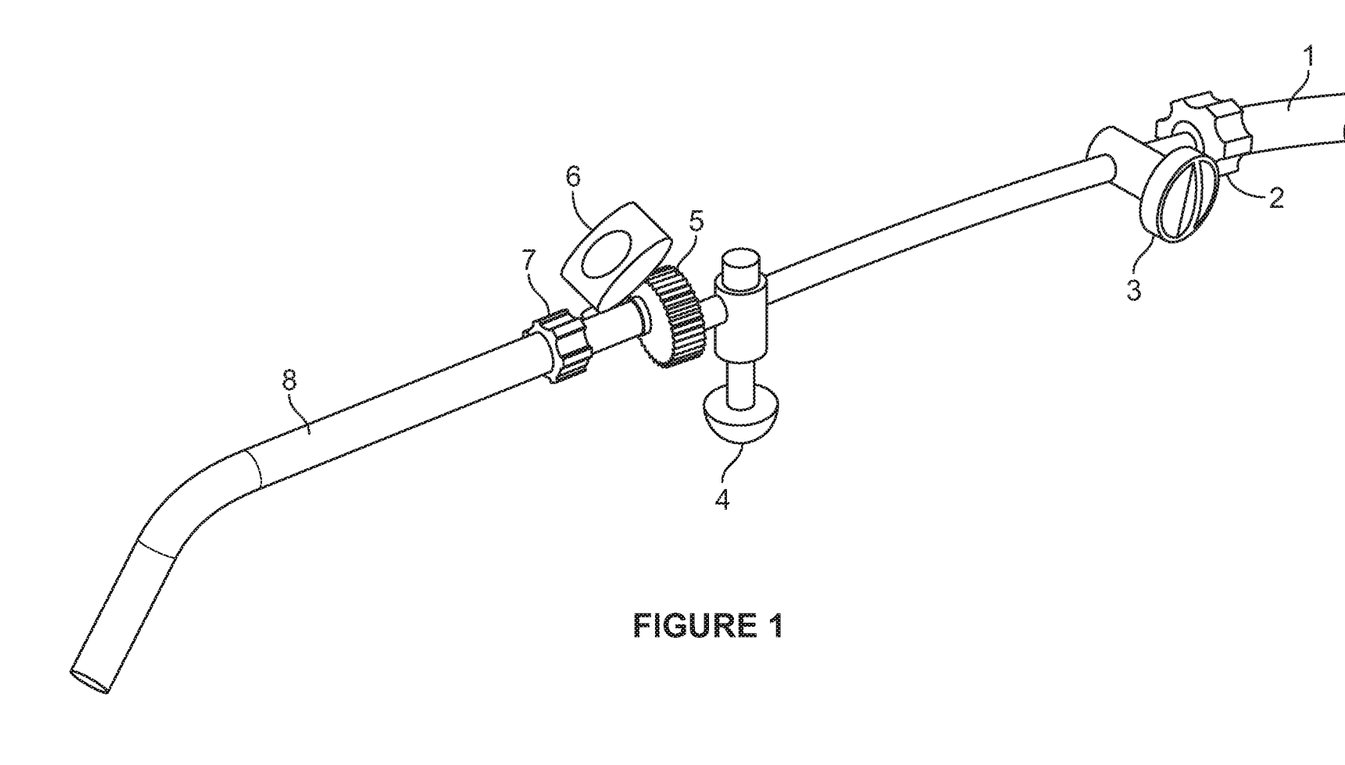
Figure 2A:
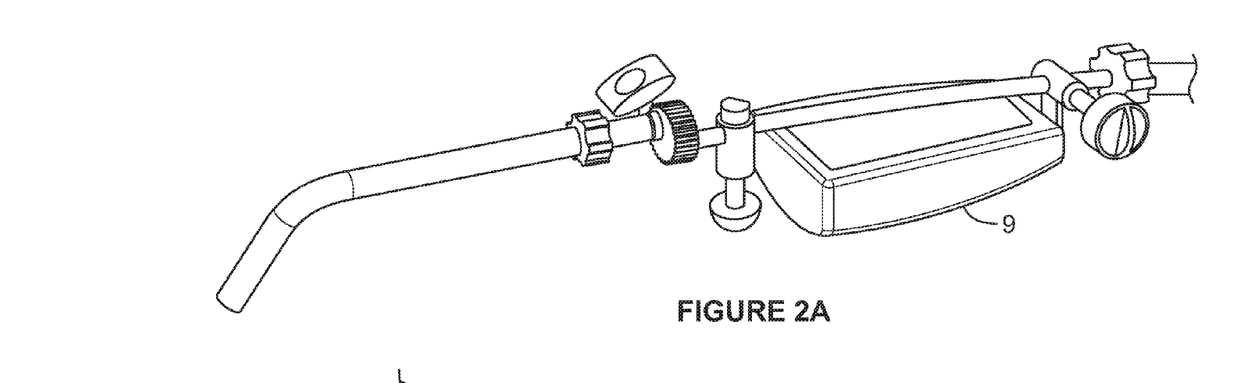
FIG. 2A shows another view of the basic structural components of one embodiment of the device of the present invention with one embodiment of a reservoir or other substances container (9).
Figure 2B:
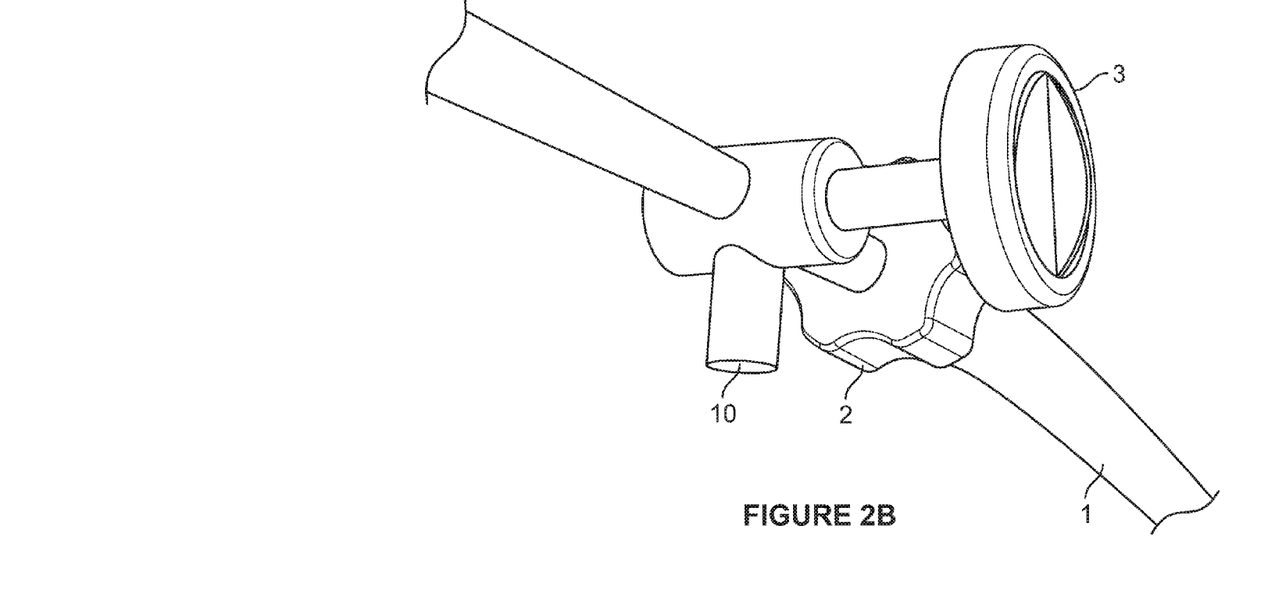
FIG. 2B shows a close up view of the water valve (2) and other substances flow valve (3). Also shown is one embodiment of an input connection for the other substances reservoir or container (10) wherein such substance is introduced into the water line prior to any entry into the hydro pulse chamber.
Figure 3A:
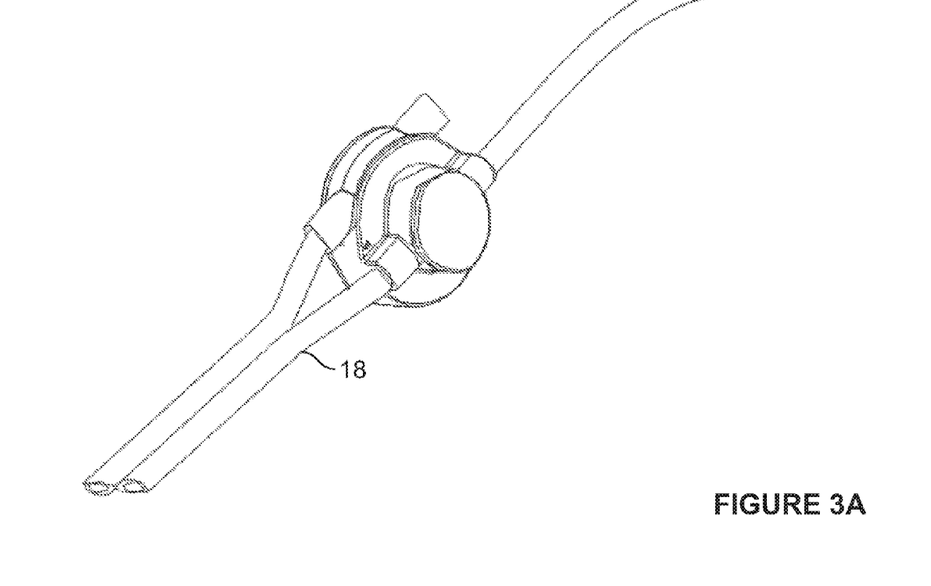
Figure 3B:
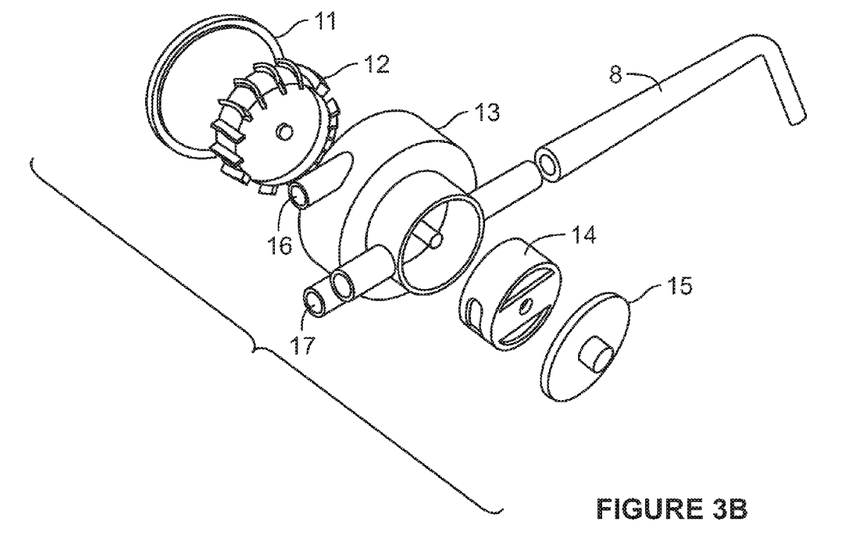
Figure 4A:
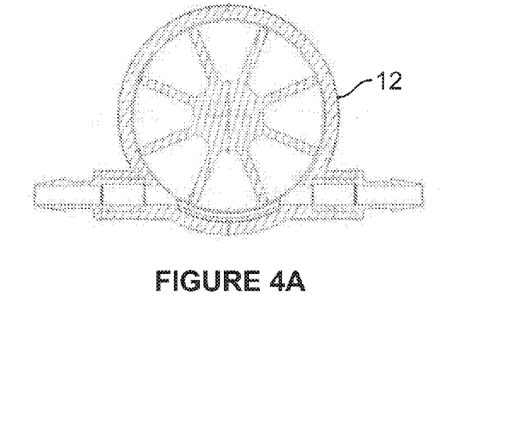
FIGS. 4A-4C show close up views of one embodiment of the hydro-pulse mechanism shown in FIGS. 3A and 3B.
Figure 4B:
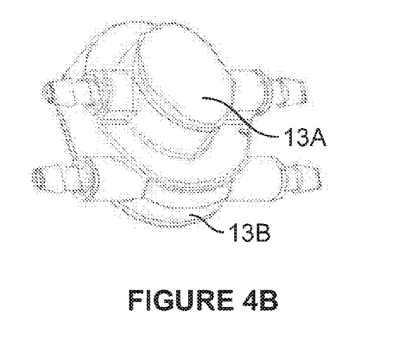
Figure 4C:
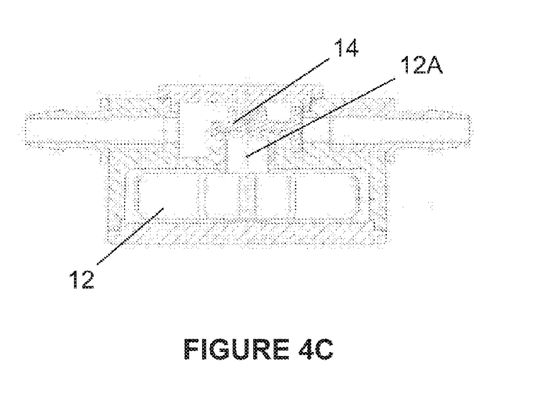
Figure 5A:
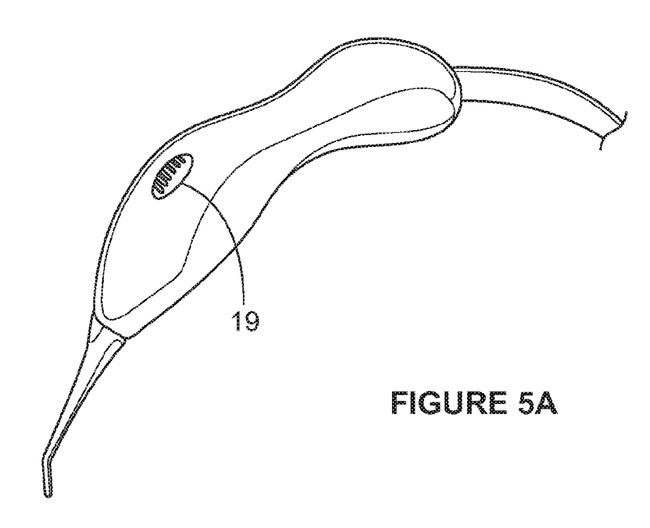
FIG. 5A shows another embodiment of the device of the present invention with an ergonomic and aesthetically pleasing housing with one on-off button (19).
Figure 5B:
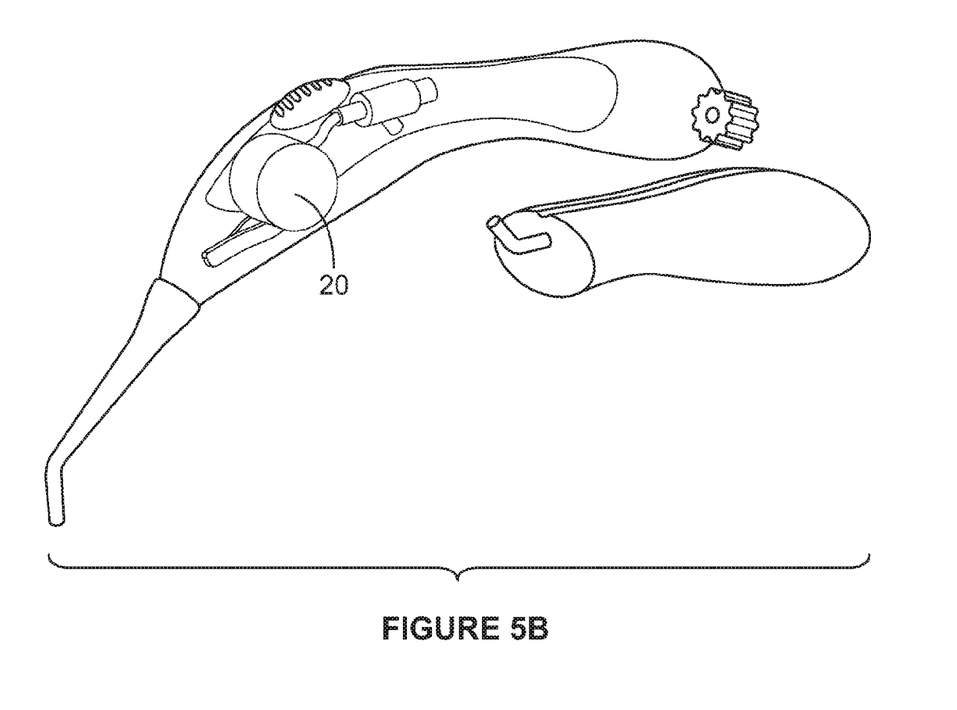
FIG. 5B shows one embodiment of the device of the present invention showing how the hydro-pulse chamber (20) fits inside such a housing.
Figure 6A:
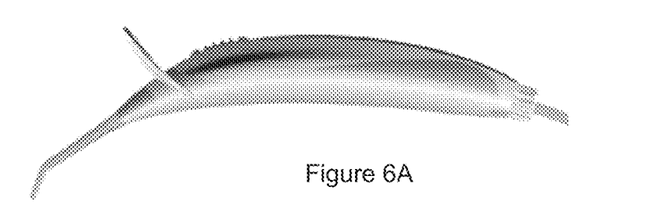
FIG. 6A-6C show different perspective views of another embodiment of the device of the present invention showing an ergonomic and aesthetically pleasing housing with a splash guard (21).
Figure 6B:
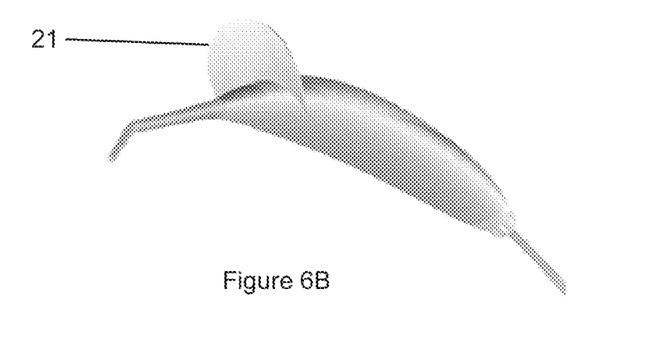
Figure 6C:
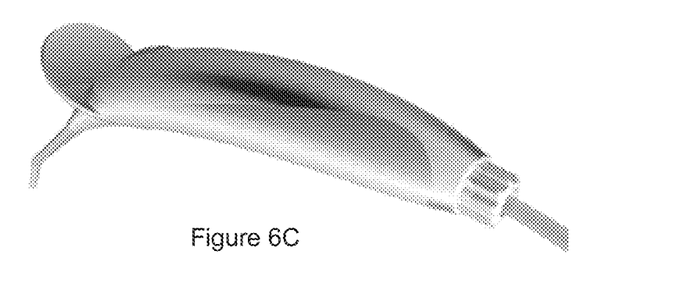
Figure 7:
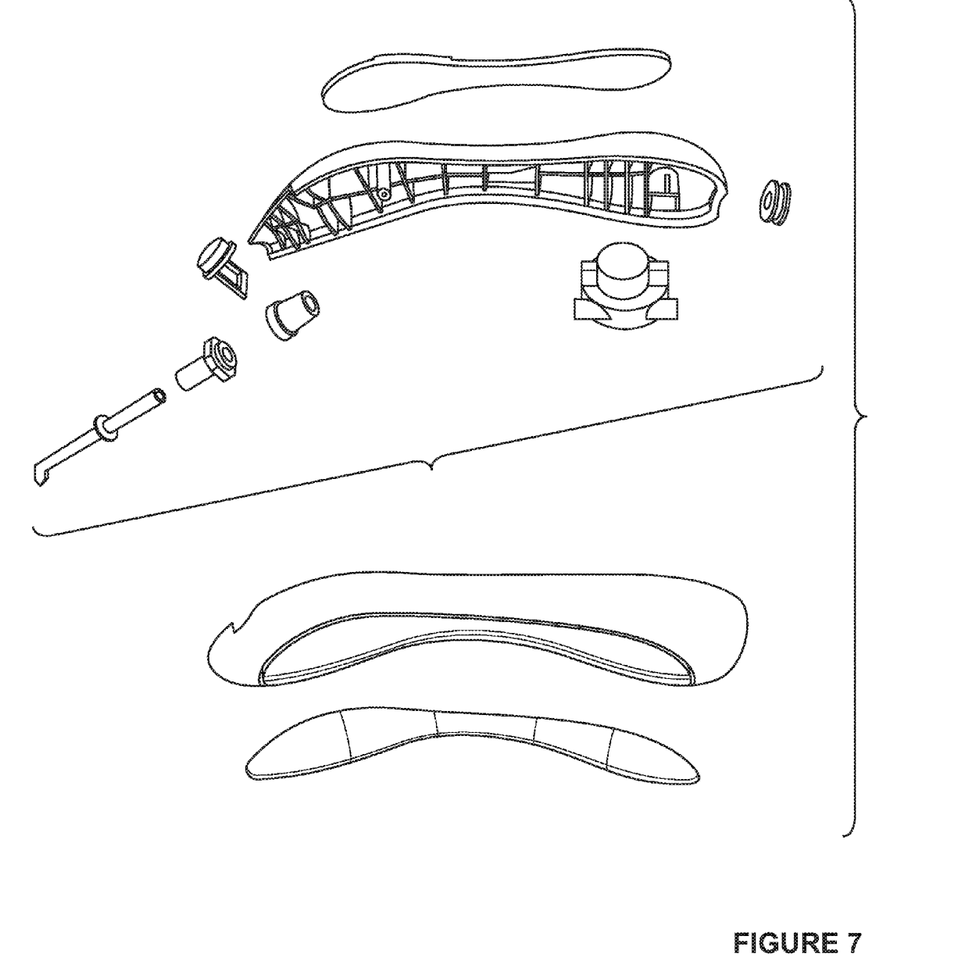
FIG. 7 shows another embodiment of the device of the present invention showing a schematic of an alternative placement of the hydro-pulse module within the housing.
Figure 8:
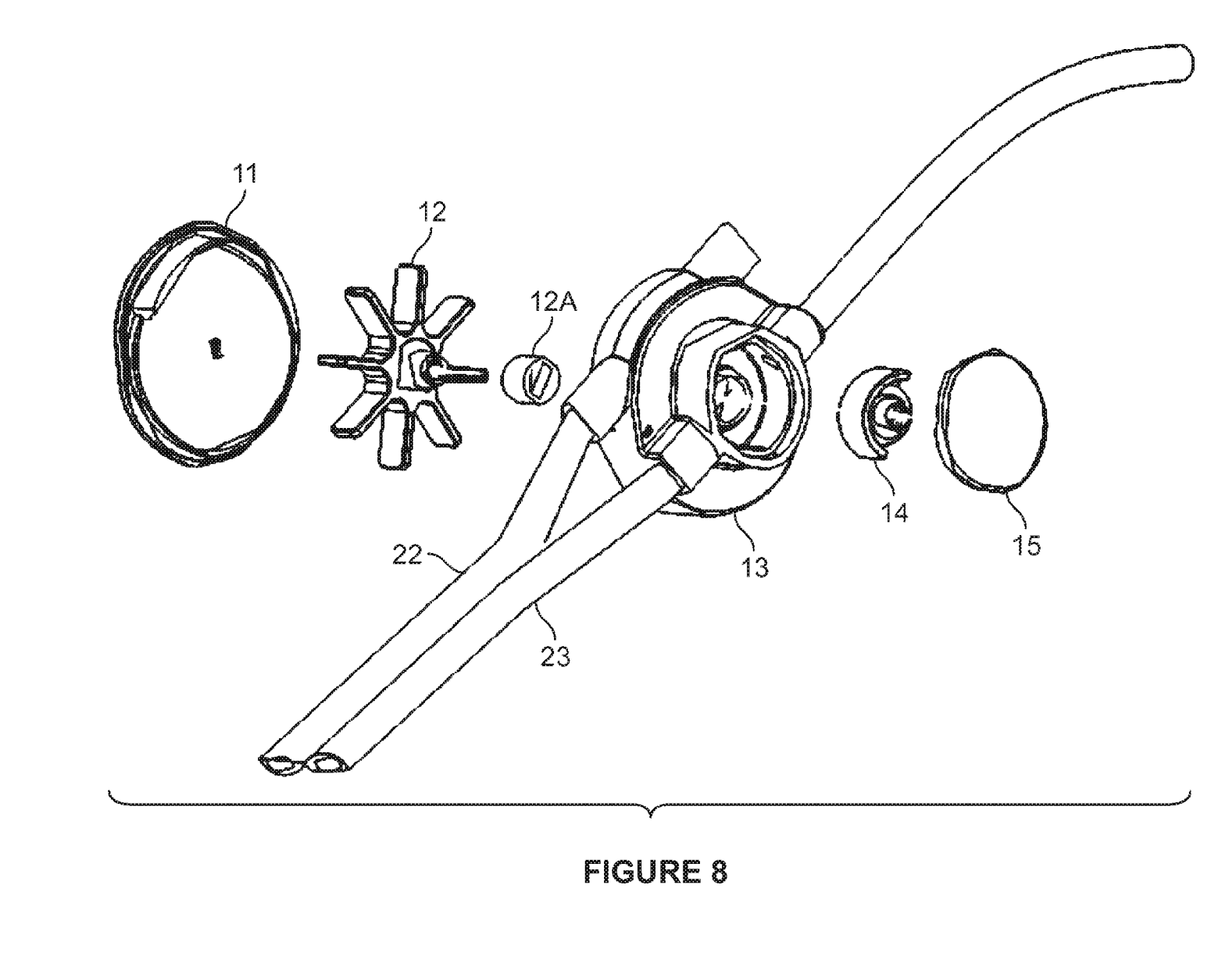
FIG. 8 shows another embodiment of the hydro-pulse mechanism depicting alternative configurations of the hydro wheel housing (13), pulse wheel (14), paddle wheel (12), axis connector (12A) and covers (11, 15) and the water inlet outlet tubes (22, 23).
Figure 9:
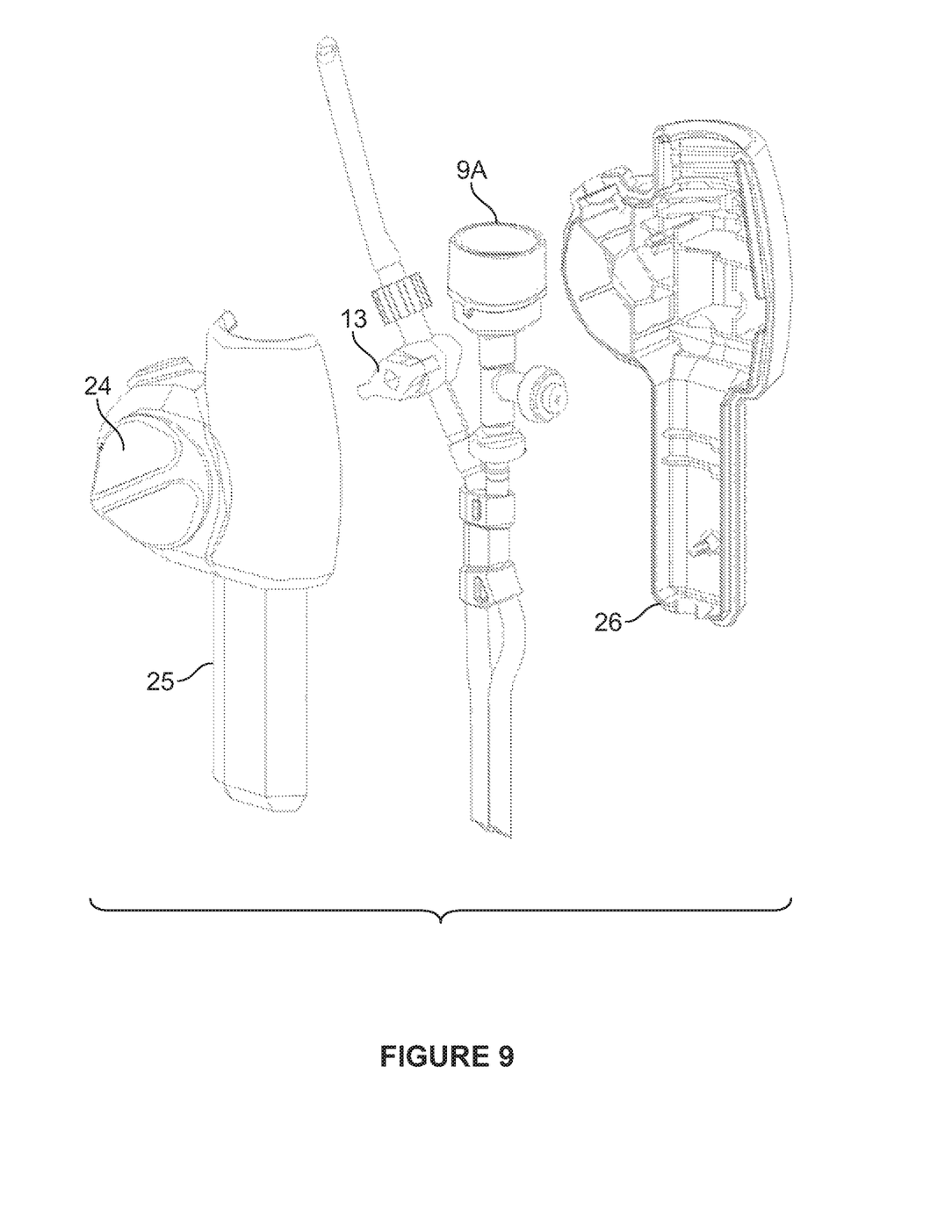
FIG. 9 shows another embodiment of the device of the present invention with an alternative placement and configuration for entry of reservoir substances (9A) and the configuration of the hydro pulse mechanism and housing (13) as they would fit within right and left assembly housing covers (25 and 26) and having an externally placed operator selector knob (24).
Figure 10:
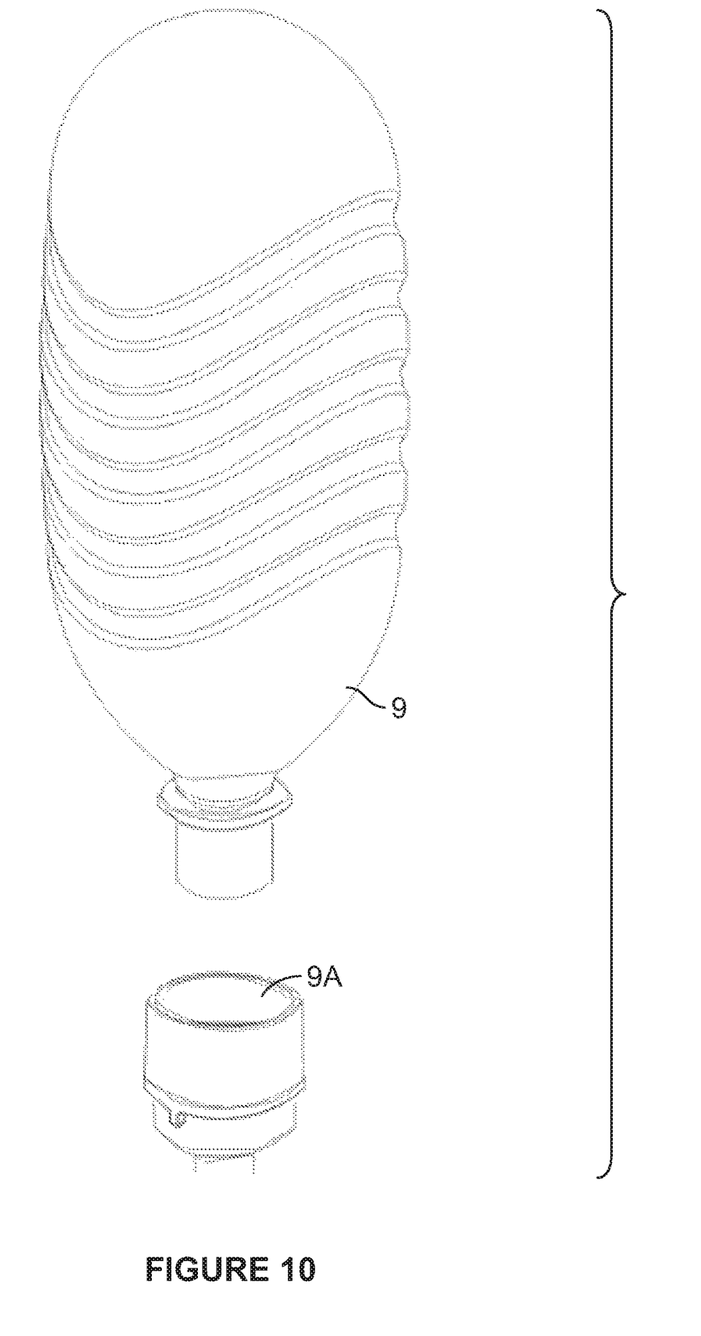
FIG. 10 shows another embodiment of the device of the present invention depicting how the reservoir (9) would attach to introduce its substance(s) into an entry port (9A).
Figure 11:
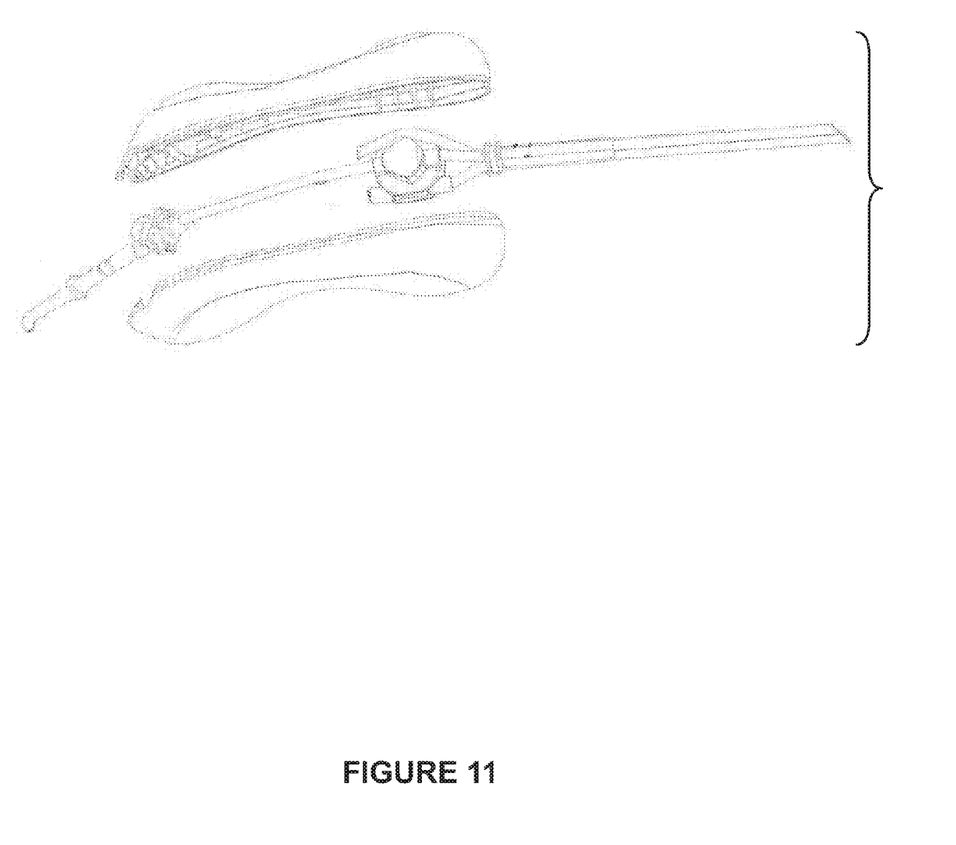
FIG. 11 shows another embodiment of the device of the present invention depicting how the components of embodiments as described herein would be assembled into an aesthetically pleasing and ergonomic housing.
Figure 12:
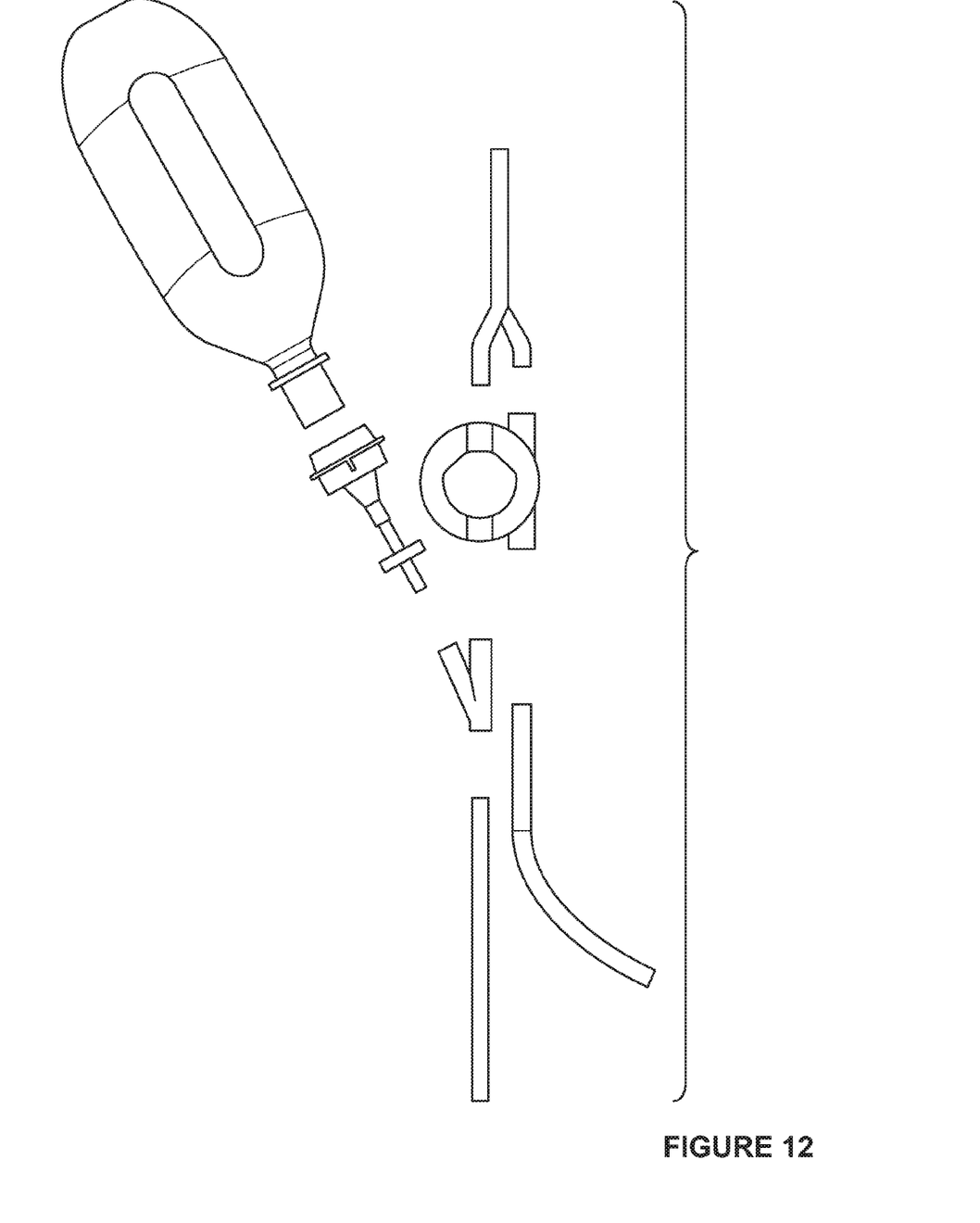
FIG. 12 shows one embodiment of the device of the present invention and potential paths of water flow wherein the reservoir substances enter the water stream after the hydro pulse module.
Figure 13:
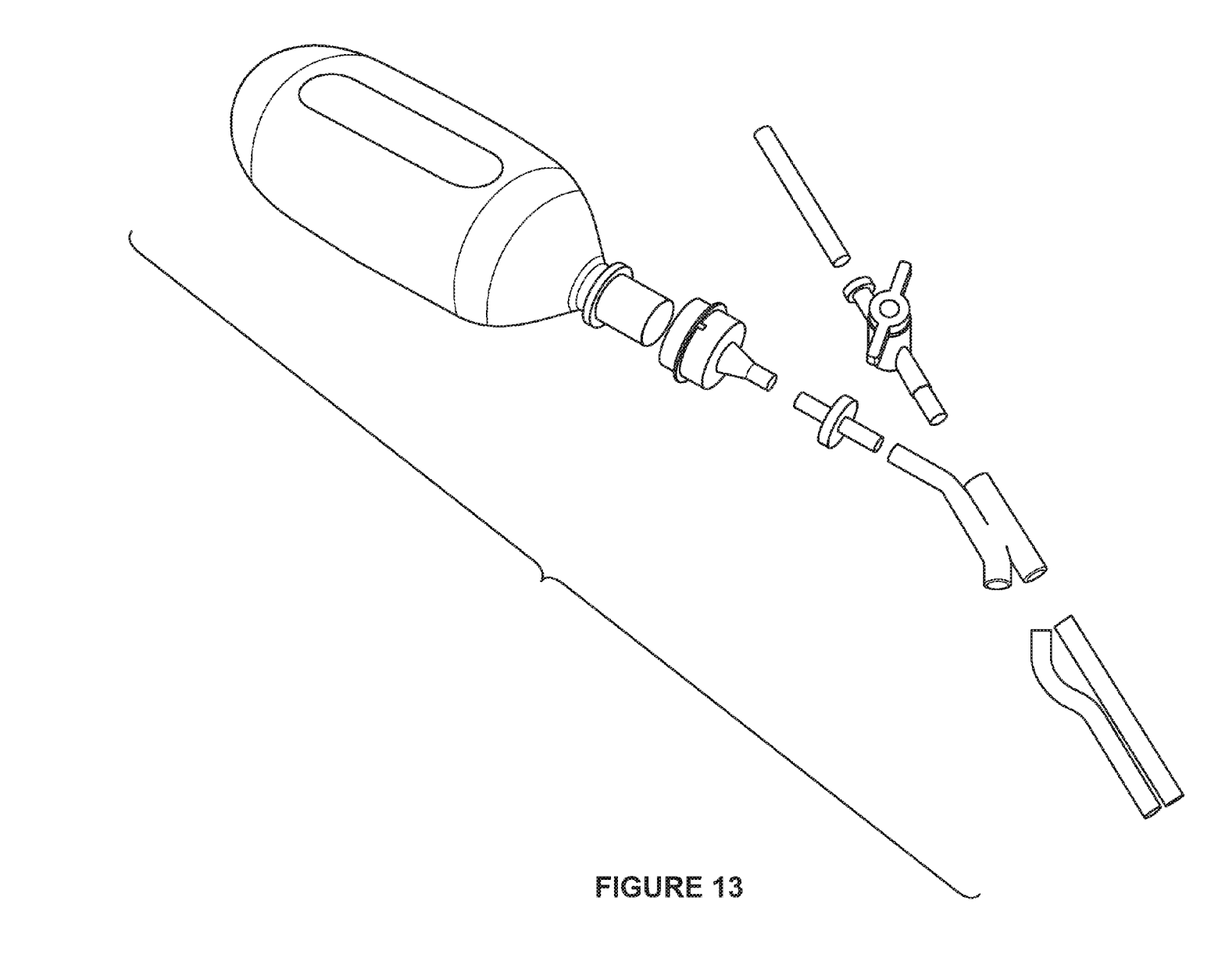
FIG. 13 shows another embodiment of the device of the present invention and potential paths of water flow wherein the reservoir substances enter the water stream before the hydro pulse module.

For clarity of disclosure, and not by way of limitation, the detailed description of the invention is divided into the following subsections that describe or illustrate certain features, embodiments or applications of the present invention.

The Device of the Present Invention

In one embodiment, the present invention provides an oral hygiene device comprising:
i. a fitting for connection to a water supply further comprising a valve for engaging the water flow into said device;

ii. a hydro pulse module further comprising a paddle wheel and a water pulsing wheel contained within a housing wherein said paddle wheel and said water pulsing wheel rotate simultaneously when engaged along a central axis;

iii. a nozzle; and iv. a nozzle valve.

In another embodiment, the present invention provides an oral hygiene device as described further comprising a reservoir for delivery of desired substances into the water flow prior to said water flow through the nozzle.

In one embodiment, the reservoir would be an interchangeable hydro-cassette containing fluid substances and introduced into the water line via a siphon and valve.

In one embodiment, the reservoir may be encased within a larger housing encasing the entire oral hygiene device.

In one embodiment, the reservoir would be integral with the overall housing design.

In one embodiment, the reservoir would contain dry ingredients that would be dissolved into the water flow.

In one embodiment, the reservoir would contain compartments for introduction of multiple substances at the choice of the operator.

In one embodiment, the reservoir r would further comprise an adjustment valve for any or all of the substances to be introduced into the water flow to control the concentration of such substance in the water flow.

In one embodiment, the reservoir would be a removeable squeeze bottle.

In one embodiment, the device would further comprise a variable valve that controls water pressure and the flow of liquid from the water source and a two-part connector that splits the flow of water and injects the reservoir substance into one water line leading directly to the pulsing wheel chamber and allows water to pass directly to the turbine paddle wheel side of the hydro pulse chamber. This connector incorporates a reduced size orifice in the whitener side of the connector and connects at an angle resulting in reduced pressure where the whitener joins the main water line. The pressure drop at the end of the connector means the reservoir substance is injected into the water stream at reduced pressure, and goes directly to the pulse side of the hydro pulse module and ultimately pulsed onto the teeth and gums.

In one embodiment, the hydro pulse module may be removed from the handset and located within the external reservoir squeeze bottle assembly thereby simplifying the hydraulic attachments and allowing the reservoir substance to be introduced after the hydro pulse module, thereby avoiding any negative effects associated with any particular reservoir substance passing through the hydro pulse module.

In one embodiment, the oral hygiene device would have replaceable and/or rotatable tips. Such tips may include various styles and/or end tips for use specifically with flossing, teeth whitening, and the like.

In one embodiment, the water supply connection would be in an ordinary shower, said fitting adapted to fit between the water supply and the shower head.

In one embodiment, the oral hygiene device would have a water off/on control such that once the water supply is turned on, the water flow would be controlled to the oral hygiene device.

In one embodiment, the hydro pulse module would operate by having the water flow rotate the paddle wheel which in turn would rotate the water pulsing wheel which when aligned properly in the housing would allow water to flow through the nozzle and when misaligned would prevent water flow through the nozzle.

In one embodiment, the hydro pulse module would have replaceable water pulsing wheels for different number of times of proper alignment allowing water flow through to the nozzle per 360° rotation.

For example, in one embodiment the water pulsing wheel would have only one through hole that would align properly every 180° rotation and provide a water pulse twice per revolution.

In one embodiment, the water pulse wheel through holes would contain an aeration function which would reduce the overall water required and increase the effectiveness of teeth cleaning.

In one embodiment, such aeration would be introduced in the water pulse wheel by a fine screen.

In one embodiment, the fine screen would be located in the nozzle or between the nozzle and the hydro pulse mechanism.

In one embodiment, the screen would be of various mesh sizes for variable aeration.

In one embodiment, such water aeration function would be variably adjusted.

In one embodiment, the water in line is divided into two separate lines entering into the hydro pulse module wherein one line enters into the paddle wheel compartment and one line enters into the pulse wheel compartment.

In one embodiment, the chamber within the hydro pulse module that contains the paddle wheel is completely separate from the chamber that contains the pulse wheel except that the paddle wheel and the pulse wheel are connected via an axle that penetrates both chambers, However, water is restricted from flowing between the chambers.

In one embodiment, this water line division would occur prior to the delivery of the reservoir substances such that those substances are not wasted in the turning of the paddle wheel, but only delivered through the water pulse wheel.

In one embodiment, the oral hygiene device would further comprise a splash guard to protect the face and eyes during operation.

In one embodiment, parts of the oral hygiene device will be molded from plastic.

In one embodiment, parts of the oral hygiene device will be molded from metal.

In one embodiment, parts of the oral hygiene device may be made from any non-corrosive, hygienic material suitable for containing water pressure and delivering a precision stream of water and other substances as disclosed herein.

In one embodiment, parts of the oral hygiene device may be made from any combination of materials.

EXAMPLES

For clarity of disclosure, the following examples are based on this device being attached in a typical shower environment. One of ordinary skill in the art will appreciate the many embodiments of the device of the present invention, for example, and not by way of limitation, installation at a bathroom sink.

In a typical installation, installation would require simply unscrewing a shower head from the shower nozzle and screwing the fitting of the device of the present invention in place and then screwing the shower head back on into a specially adapted fitting.

Thereafter, the device of the present invention would work by simply turning the shower water on and depressing a button on the device to make water flow through it and releasing the button to stop water from flowing through it.

When this device is used in the shower, there would be no need for worry about the mess of spilled water or other messes.

In a preferred embodiment, one or more reservoirs would contain one or more a liquid substances such as mouthwash, oral antiseptic, teeth whitener, gum health substances and the like, any or all of which can be siphoned into the water flow according to the foregoing description that will be delivered through the nozzle.

The operator would then direct the nozzle tip at a space in the mouth for cleaning such as directly at the teeth or in between teeth or at the gums and then depress the button to begin the flow of treated water.

At any time, the operator would simply release the button and the flow would stop.

By turning off the shower, water flow to the inlet line would cease and release any pressure in the device.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Each and every feature described herein, and each and every combination of two or more of such features, is included within the scope of the present invention provided that the features included in such a combination are not mutually exclusive.

What is claimed is:

1. An oral hygiene device comprising:
   (i) a fitting for connection to a water supply further comprising a valve for engaging a water flow from said water supply into said device;
   (ii) a hydro pulse module further comprising a paddle wheel housed in a first chamber and a water pulsing wheel housed within a separate second chamber wherein the paddle wheel and first chamber are configured to have no pulsing function and the water pulse wheel is configured to have at least one water through hole for allowing water flow through it only when the at least one through hole is aligned properly with a corresponding outlet contained within the separate second chamber and wherein the first and second chambers are physically isolated such that water flow is restricted from passing from one chamber to the other and wherein said paddle wheel and said water pulsing wheel rotate simultaneously when engaged along a central axis and said water flow is configured to enter into both the first and second chambers simultaneously;
   (iii) a nozzle; and
   (iv) a nozzle valve.

2. The device of claim 1 further comprising a reservoir for delivery of desired substances into the water flow prior to said water flow through the nozzle.

3. The device of claim 1 further comprising a reservoir for delivery of desired substances into the water flow prior to entrance into the hydro pulse module and prior to said water flow through the nozzle.

4. The device of claim 1 further comprising a reservoir for delivery of desired substances into the water flow after exiting the hydro pulse module and prior to said water flow through the nozzle.

5. The device of claim 2 wherein said substances may be any one or more substances chosen from the following group: whitener, mouthwash, oral antiseptic, antibiotic, vitamins, flavoring, and fluoride.

6. The device of claim 2 wherein the reservoir is interchangeable.

7. The device of claim 2 further comprising an adjustment valve for choosing the concentration of substance delivered into the water flow.

8. The device of claim 1 further comprising an off/on button valve to control the flow of water.

9. The device of claim 1 further comprising a splash guard.

* * * * *